US011494172B2

(12) United States Patent
Cronrath et al.

(10) Patent No.: US 11,494,172 B2
(45) Date of Patent: *Nov. 8, 2022

(54) MEDICAL SOFTWARE DOWNLOAD TO MOBILE PHONE

(71) Applicant: Roche Diabetes Care, Inc., Indianapolis, IN (US)

(72) Inventors: Christoph Cronrath, Lautersheim (DE); Fernando Andreu, Barcelona (ES); Alberto Val Vicente, Grinon (ES)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/830,190

(22) Filed: Jun. 1, 2022

(65) Prior Publication Data
US 2022/0291910 A1 Sep. 15, 2022

Related U.S. Application Data

(63) Continuation of application No. 17/038,823, filed on Sep. 30, 2020, which is a continuation of application
(Continued)

(30) Foreign Application Priority Data

Apr. 12, 2005 (EP) .................................... 05380070

(51) Int. Cl.
*G06F 9/44* (2018.01)
*G16H 50/20* (2018.01)
(Continued)

(52) U.S. Cl.
CPC ............... *G06F 8/60* (2013.01); *G16H 10/40* (2018.01); *G16H 40/40* (2018.01); *G16H 40/67* (2018.01)

(58) Field of Classification Search
CPC .......... G06F 8/60; G16H 10/40; G16H 40/40; G16H 40/67
See application file for complete search history.

(56) References Cited

U.S. PATENT DOCUMENTS

| 5,307,263 A | 4/1994 | Brown |
| 5,544,661 A | 8/1996 | Davis et al. |

(Continued)

FOREIGN PATENT DOCUMENTS

| DE | 602 25 006 T2 | 3/2009 |
| EP | 0 880 936 A2 | 12/1998 |

(Continued)

OTHER PUBLICATIONS

International Preliminary Report on Patentability, PCT/EP2006/061554, dated May 15, 2007, 11 pages.
(Continued)

*Primary Examiner* — Maroun P Kanaan
(74) *Attorney, Agent, or Firm* — Bose McKinney & Evans LLP

(57) ABSTRACT

A method for monitoring medical data is disclosed, the method being applicable to a system comprising a portable medical device, a mobile communications device, and, optionally, a medical care server. The portable medical device and the mobile communications device each comprise at least one interface for data transfer. The method comprises a step of establishing a download link between the mobile communications device and a download server. The method comprises a step of selecting an appropriate communication software package from a plurality of communication software packages for controlling data transfer between the mobile communications device and the portable medical device from the download server. Further, the method comprises a download step for downloading communication software package from the download server to
(Continued)

the mobile communications device and a step of installation of the communication software package on the mobile communications device.

17 Claims, 3 Drawing Sheets

Related U.S. Application Data

No. 15/722,067, filed on Oct. 2, 2017, now Pat. No. 10,803,989, which is a continuation of application No. 11/911,142, filed as application No. PCT/EP2006/061554 on Apr. 12, 2006, now Pat. No. 9,811,633.

(51) Int. Cl.

| | | |
|---|---|---|
| *G06F 8/60* | (2018.01) | |
| *G16H 40/67* | (2018.01) | |
| *G16H 10/40* | (2018.01) | |
| *G16H 40/40* | (2018.01) | |

(56) References Cited

U.S. PATENT DOCUMENTS

| | | | |
|---|---|---|---|
| 5,558,638 A | 9/1996 | Evers et al. | |
| 5,678,571 A | 10/1997 | Brown | |
| 9,811,633 B2 | 11/2017 | Conrath et al. | |
| 10,803,989 B2 | 10/2020 | Conrath et al. | |
| 2002/0013613 A1 | 1/2002 | Haller et al. | |
| 2002/0178126 A1* | 11/2002 | Beck | G16H 40/67 705/2 |
| 2003/0065536 A1 | 4/2003 | Hansen et al. | |
| 2003/0114885 A1* | 6/2003 | Nova | A61N 1/08 607/2 |
| 2004/0073912 A1 | 4/2004 | Meza | |
| 2005/0005270 A1* | 1/2005 | Bucher | H04L 67/303 717/173 |
| 2005/0272464 A1 | 12/2005 | Ishikawa et al. | |
| 2006/0031094 A1 | 2/2006 | Cohen et al. | |
| 2018/0025120 A1 | 1/2018 | Conrath et al. | |

FOREIGN PATENT DOCUMENTS

| | | |
|---|---|---|
| EP | 0 970 655 A1 | 1/2000 |
| EP | 1 394 707 A1 | 3/2004 |
| JP | 2002-17693 A | 1/2002 |
| JP | 2004-135759 A | 5/2004 |
| WO | WO 95/32480 A1 | 11/1995 |
| WO | WO 97/28736 A1 | 8/1997 |
| WO | WO 98/31275 A1 | 7/1998 |
| WO | WO 99/46718 A1 | 9/1999 |
| WO | WO 02/100262 A1 | 12/2002 |
| WO | WO 03/067484 A1 | 8/2003 |
| WO | WO 2004/027676 A2 | 4/2004 |

OTHER PUBLICATIONS

International Search Report and Written Opinion of the International Searching Authority, PCT/EP2006/061554, dated Jun. 12, 2006, 8 pages.

* cited by examiner

MEDICAL SOFTWARE DOWNLOAD TO MOBILE PHONE

CROSS-REFERENCE TO RELATED APPLICATIONS

The present application claims priority to and is a continuation of U.S. patent application Ser. No. 17/038,823, entitled "MEDICAL SOFTWARE DOWNLOAD TO MOBILE PHONE," filed Sep. 30, 2020, which claims priority to U.S. patent application Ser. No. 15/722,067, now U.S. Pat. No. 10,803,989, entitled "MEDICAL SOFTWARE DOWNLOAD TO MOBILE PHONE," filed Oct. 2, 2017, which claims priority to and is a continuation of U.S. patent application Ser. No. 11/911,142, now U.S. Pat. No. 9,811,633, entitled "MEDICAL SOFTWARE DOWNLOAD TO MOBILE PHONE," filed Aug. 5, 2008, which is a national stage entry of PCT Application No. PCT/EP2006/061554, entitled "MEDICAL SOFTWARE DOWNLOAD TO MOBILE PHONE," filed Apr. 12, 2006, the entire disclosures of which being hereby expressly incorporated herein by reference.

FIELD OF THE DISCLOSURE

The disclosure relates to a method for monitoring medical data using a portable medical device and a mobile communication device. The disclosure further relates to a system for monitoring medical data, the system comprising a portable medical device and a mobile communications device. The method and the system according to the disclosure may be applied, e.g., for monitoring a glucose level information, a blood pressure information, a cholesterol level information, and/or a coagulation information, or may be applied to information transfer concerning an insulin medication. The method and the system according to the disclosure may be applied within the framework of a homecare medical system, e.g. a homecare medical system comprising one or more healthcare centers.

BACKGROUND

In many fields of medical treatment and healthcare, a monitoring of certain body functions is required. Thus, e.g., for patients suffering from diabetes, a regular check of the blood glucose level forms an essential part of the daily routine. The blood glucose level has to be determined fast and reliably several times per day, in order to initiate a responsive medication in case certain limits are exceeded. In order not to unduly disturb the daily routine of the patient, in many cases portable medical devices are used. A large number of portable medical devices for monitoring various body functions are commercially available.

Nevertheless, the use of portable medical devices involves some risks, which are mainly due to the fact that the handling of the portable medical devices is sometimes complicated, which, mainly for elderly patients or infants, may lead to handling failures and, thus, to the risk of insufficient or even wrong monitoring results. Further, since most of the patients handling the portable medical devices have not undergone a medical training, the interpretation of the medical data gained by using the portable medical devices is not always easy. Therefore, often, the patients are required to see their doctors or any other health consultants in short time-intervals on a regular basis.

In order to reduce the frequency of necessary visits to the doctor or even hospitalizations, the idea of home-care has gained popularity over the recent years. Thus, e.g. the availability of mobile communications devices, such as cell phones, as well as the omnipresence of communication networks, such as the internet or wireless communication networks, has led to the development of medical care systems allowing for monitoring patients at home, using a portable medical device and a data transfer system for transferring medical data to a health care center.

U.S. Pat. No. 5,544,661 discloses a patient monitoring system which includes a portable device and a central station. The portable device includes an ECG and a photoplethysmograph connected to the patient, an arrhythmia analysis apparatus, an expert system for determining if a pre-established critical parameter set has been exceeded, and a wireless wide-area communication device for automatically contacting the central station via a public cellular phone network when the critical parameter set has been exceeded. When the central station is contacted, the patient's ECG waveforms, measurements, and trends are sent to the central monitoring station and a 2-way voice channel between the patient and the central station is automatically opened.

The components of the system have to be adapted by integrating suitable hardware and software modifications into standard devices, in order to be applied within the mobile patient monitoring system. Thus, for many "every day" purposes, such as blood pressure monitoring or blood glucose level monitoring, the system described in U.S. Pat. No. 5,544,661 exceeds the frame of allowable costs for a health monitoring system.

WO 97/28736 discloses a method for monitoring the health of a patient by utilizing measurements. The method comprises a supply of the results of the measurements to a person treating the patient via a communications device utilizing a wireless data transmission link to a data processing system available to the person monitoring the patient's health. The patient's health is monitored by means of the data stored in the data processing system. Specifically, WO 97/28736 relates to the self-care and monitoring of the health of a diabetes patient.

Similarly, EP 0970655 A1 discloses a portable apparatus of reduced size, which has an analyzer for analyzing the glucose in the blood and for providing a series of values. The values can be processed in situ by a microprocessor and displayed on a screen of a personal computer connected to the glucose analyzer. The telematic control system for patients provided with the apparatus would provide that the data calculated in the portable apparatus would be transmitted to a central unit for the remote interpretation of the data through a mobile telephone which is also interconnected with the microprocessor and the analyzer. The system disclosed in EP 0970655 A1 is made up of four basic elements: a central unit, a laboratory terminal, a doctor's unit, and a patient's terminal. The patient's terminal is made up of a blood glucose auto analyzer, a compatible personal computer and a digital mobile telephone apparatus (GSM), which are integrated in a single apparatus.

Both the system disclosed in WO 97/28736, and the system disclosed in EP 0970655 A1 utilize devices of every day use, such as personal computers and digital mobile phones, in order to exchange medical information between the patient and a health care center. Nevertheless, the systems disclosed in WO 97/28736 and EP 0970655 A1 still involve several disadvantages. Thus, the mobile digital phones have to be specifically adapted, in order to be applicable within the health monitoring system. Thus, the mobile phone has to be equipped with suitable software and/or hardware, in order to be able to communicate with the blood glucose auto analyzer. For this purpose, in many cases, the mobile digital phone has to be shipped to a specialized health care provider, in order to be disassembled and in order to, e.g., have a software flashed into the cell phone's EEPROM. Alternatively or additionally, the software can be programmed by exchanging the SIM-card using a new SIM-card containing a suitable software. This method is rather time-consuming and costly. Further, the flexibility of this method is rather low, since the service lifetime of devices such as digital mobile phones or certain medical monitoring devices in many cases does not exceed several months. In this case, after replacing the digital mobile phone or the portable medical device, the routine of programming the portable medical device and/or the digital mobile phone has to be repeated, thus further increasing costs. Further, the systems disclosed in the state of the art, are not designed to be "open" to new "members" of the system, such as new portable medical devices. Therefore, in most cases, only certain pairs of portable medical devices and digital mobile phones can be combined.

SUMMARY

The method according to the disclosure is applicable for monitoring medical data using a portable medical device and a mobile communications device, each of these devices comprising at least one interface for data transfer. In this context, the expression "monitoring" comprises a wide variety of meanings. Thus, monitoring may comprise an exchange of data, including medical data, an evaluation and/or validation of data, (pre-) processing of data, visualization of data, bringing data to someone's attention, and/or initiating certain processes, such as warning functions or medical treatment, in case predetermined conditions are fulfilled by the data.

The mobile communications device may comprise basically any type of mobile communications device or any combination of mobile communication devices. The mobile communications device may comprise a mobile phone and/ or a personal digital assistant (PDA) and/or a handheld computer. The mobile communications device is equipped to communicate via a mobile communications network.

The portable medical device may comprise basically any portable medical device, including a medical device for monitoring a patient's medical data and/or applying a medical treatment to a patient. Further, a combination of portable medical devices may be used. The portable medical device may comprise a glucose meter, such as a blood glucose meter, and/or a cholesterol meter, and/or a blood pressure meter, and/or a coagulation meter, and/or an insulin pump.

The method comprises the following steps, which do not have to be performed in the order given below. Further steps not listed below may be performed additionally. Steps may be performed repeatedly or several steps may be performed in parallel.

In one embodiment, a download link is established between the mobile communications device and a download server during the first process step. The download link comprises a wireless download link, e.g. using a public mobile communications network, such as a digital wireless network, e.g. a GSM network. The initiation of the establishment of the download link between the mobile communications device and the download server may be performed by several possible ways. Thus, the patient may call a pre-determined telephone number, in order to initiate the establishment of the download link. Further, an electronic message, such as a Wireless Application Protocol (WAP) Push Message may be transmitted to the mobile communications device, e.g. by the download server, the electronic message comprising a download address defining a download location on the download server. This download address may, e.g. comprise an Internet Protocol (IP) address and/or a Uniform Resource Locater (URL). The download server may be part of a health care center or may be part of a server's system provided by a mobile communications device manufacturer and/or a portable medical device manufacturer.

In a second step, a communication software package is chosen from a plurality of communication software packages for controlling a data transfer between a mobile communications device and a portable medical device stored on the download server. This choice of a communication software package depends on the type of mobile communications device and/or on the type of portable medical device used by the patient (user). Thus, e.g. the user may select from the list of mobile communications device types and a list of types of portable medical devices. Alternatively, or additionally, the type of the user's mobile communications device may be detected automatically by the download server. For this purpose, the method may include a step of transmitting "type information" comprising information of the type of the mobile communications device to the download server. This embodiment of the disclosure allows for the download server to automatically narrow the choice of communication software packages offered to the user, in a way, that only communication software packages suited for the user's type of mobile communications device are offered. In this case, the user only has to select from a list of portable medical devices, in order to download a communication software package suited for the communication between the user's mobile communications device and the user's portable medical device.

The communication software package comprises a software package, e.g. a self-installing software package, for controlling the data transfer between the mobile communications device and the portable medical device. Therefore, as denoted above, both the mobile communications device and the portable medical device each comprise at least one interface for data transfer. This interface comprises at least one interface for wireless data transfer. Thus, e.g. an infrared data transfer, using an Infrared Data Association (IrDA) standard link, can be used. Alternatively or additionally, a radio frequency data transfer link may be used, comprising an interface for Bluetooth data transfer and/or for near field communication (NFC) data transfer. Nevertheless, alternatively or additionally, hardware-based data transfer means may be used, such as a data transfer by communication cables or interface cables. Thus, using the communication software package, data may be exchanged between the portable medical device and the mobile communications device uni-directionally or bi-directionally. Thus, medical data can be transmitted from the portable medical device to the mobile communications device. In turn, control signals, such as signals indicating a command for starting a measurement, as well as other data, can be transmitted from the mobile communications device to the portable medical device.

Further, the method according to the disclosure comprises a step of downloading the communication software package from the download server to the mobile communications device. The communication software package may e.g. be stored in a storage medium within the mobile communications device and/or on a separate computer device. In a further step, the communication software package is installed on the mobile communications device. As explained above, the installation step may be performed automatically or may involve a user-initiated action. Thus, e.g. before installing the communication software package, the user may be asked permission to initiate the installation, e.g. by activating a certain key of the mobile communications device.

The method according to the disclosure offers a high flexibility regarding the choice of the mobile communications device and the choice of the portable medical device. The patient or user may easily switch between various types or models of devices. In case of a device change, the user only has to download a new communication software package from the download server, in order to allow for the communication between the mobile communications device and the portable medical device he intends to use. Hardware changes may not be required, since many portably medical devices and mobile communications devices are using standardized interfaces, such as IrDA interfaces. Thus, a shipment of the mobile communications device to a provider, in order to exchange software modules and in order to adapt the mobile communications device for communication with a specific portable medical device, is not necessary any longer.

For downloading the communication software package from the download server, simple download procedures can be used, such as procedures known from downloading ring tones to cell phones from a provider's server. Thus, the method according to the disclosure significantly increases the applicability of mobile health care systems and, thus, reduces health care costs and improves patient's monitoring in everyday life.

The method according to the disclosure may be extended or improved by many ways. Thus, the method may comprise a step during which at least one first medical information is exchanged between the portable medical device and the mobile communications device by means of data transfer. Thus, at least one diagnostic information may be exchanged, for example by transmission from the portable medical device to the mobile communications device. The first medical information may comprise several types of information. Thus, as described above, the data transfer may be unidirectional in each direction between the mobile communications device and the portable medical device or may be bidirectional. Thus, the mobile communications device may be used in order to initiate measurements and/or to program the portable medical device. Further, medical information may be transmitted from the portable medical device, such as measurement information of medical measurements. Thus, a glucose level information, such as a blood glucose level information and/or a blood pressure information, and/or a cholesterol level information, and/or a coagulation information may be transmitted. Further, a measuring time, such as a point of time related to a measurement of a specific medical information, may be transmitted. Further, a dose information, e.g. a dose information for an insulin medication, such as a dose information for programming an insulin pump, may be transmitted, in this case in the direction from the mobile communications device to the portable medical device.

The at least one first medical information may be stored in a database on the mobile communications device. Thus, the mobile communications device may comprise a database software. This database software may, e.g. be downloaded from the same download server as the communication software package or may be downloaded from a separate download server. The way of downloading may be similar to the downloading of the communication software package as listed above. Further, the database software may even be part of the communication software package downloaded from the download server.

Additionally or alternatively to the database software, other types of software algorithms may be applied to the first medical information. Thus, at least one evaluation algorithm may be applied by the mobile communications device to the at least one first medical information. Similarly to the database software, this evaluation algorithm may be separate from or may be part of the previously listed software modules, such as the communication software package and/or the database software. Further, the at least one evaluation algorithm may be downloaded from the same download server or from a separate download server, within the same or a separate download step.

The at least one evaluation algorithm may e.g. provide an algorithm for processing or pre-processing the at least one first medical information. This processing may include a comparison of the at least one first medical information with certain user-specific limits, such as a comparison of blood glucose levels with pre-determined blood glucose level limits, and, additionally, may comprise a warning function warning a user in case certain levels are exceeded. Further, the processing of data may comprise averaging, filtering, and other similar algorithms.

Further, separately or being part of the evaluation algorithm, at least one medical user information can graphically and/or acoustically be presented to a patient by the mobile communications device. Thus, the at least one medical user information may be graphically displayed on a display, such a display integrated into the mobile communications device. Alternatively or additionally, data can be transferred to a separate computer, such as data stored in the database, which may be downloaded to a personal computer or a laptop, e.g. for the purpose of further evaluation and/or storage.

The method according to the disclosure may further be extended by adding a step of establishing an upload link between the mobile communications device and a medical care server. The medical care server may be identical or be part of the download server or may comprise a separate server. As an example, the medical care server may be part of a server system located at a hospital or a health care center. Thus, after establishing the upload link between the mobile communications device and the medical care server, at least one second medical information may be exchanged between the mobile communications device and the medical care server. This at least one second medical information exchanged between the mobile communications device and the medical care server may be identical to the first medical information described above. It may further be an extraction from the at least one first medical information, such as a selection from the first medical information considered to be relevant. Thus, the at least one first medical information may be pre-processed for the purpose of data-reduction, in order to reduce the amount of data transferred between the mobile communications device and the medical care server.

Additionally or alternatively, the at least one second medical information exchanged between the medical care server and the mobile communications device may comprise additional data, such as a user identification number or a similar data. Similarly to the communication between the mobile communications device and the portable medical device, the data exchange between the mobile communications device and the medical care server may be unidirectional in each direction or may be bidirectional. Thus, e.g. the at least one second medical information may comprise an information transmitted from the medical care server to the mobile communications device, indicating for the patient to consult his doctor, e.g. in case part of the at least one second medical information transmitted from the mobile communications device to the medical care server indicates that a critical medical condition has occurred.

The exchange of the at least one second medical information between the mobile communications device and the medical care server may, e.g., comprise an exchange of a Short Message Service (SMS) message. Thus, the amount of data exchange between the mobile communications device and the medical care server may be reduced to a minimum, by using standard SMS messages, whereby communication channel resources are freed.

The embodiment of the exchange of the at least one second medical information between the mobile communications device and the medical care server allows a full integration of the patient into a mobile health care system. The at least one medical care server may be accessible by the patient's doctor, in order for the doctor to access information on the health status of the patient at any time or anywhere. Additionally or alternatively, the medical care server may comprise evaluation means, such as evaluation algorithms, and/or database applications, in order to allow for e.g. a long term monitoring of the patient's health. Further, the health care server may transmit information to the mobile communications device on medical treatment, e.g. in response to a measured health condition, such as information on an insulin dose or an automatic warning. The insulin dose information or other medication information may be transmitted from the medical care server to the mobile communications device and, successively, from the mobile communications device to the portable medical device. Thus, the method allows for an ultra-fast reaction, which may occur automatically to critical changes of the patient's health conditions. Thus, the method according to the disclosure reduces the health care risk and reduces the cost for health care by reducing the necessity of frequent hospitalization.

Within the spirit and the scope of the disclosure, a second method for monitoring medical data using a portable medical device and mobile communications device is proposed. The portable medical device and the mobile communications device may be equipped as in the first method described above. The second method according to the disclosure comprises the following steps, which, again, do not have to be performed in the order given below. Further, additional steps not listed below may be performed and steps may be performed repeatedly and/or in parallel.

The method comprises a step of establishing a download link between the mobile communications device and a download server. Further, the method comprises choosing an upload communication software package from a plurality of upload communication software packages for uploading at least one third medical information from the mobile communications device to a medical care server. The choice of the upload communication software package depends on the type of mobile communications device used by the patient. Again, the method may comprise an automatic transmission of an information concerning the type of mobile communications device used by the patient to the download server, as described above. In the latter case, the download server may automatically select an appropriate communication software package suited for the type of mobile communications device used by the patient. Alternatively, the patient may manually select or input the type of mobile communications device he is using.

This upload communication software package is downloaded to the mobile communications device and, as described above, installed automatically or initiated by a separate user action. This second method according to the disclosure allows for the user to upload at least one third medical information to the medical care server. This at least one third medical information may, as described for the at least one second medical information, comprise part of the at least one first medical information and/or the at least one second medical information, may be identical to this information, and/or may comprise additional information. Thus, the at least third medical information may comprise a glucose level information, a blood pressure information, a cholesterol level information, a coagulation information, a measuring time, a dose information for insulin indication, and/or other types of information. The transmission of the at least one third medical information may comprise a transmission of a Short Message Service (SMS) message, similar to the first method according to the disclosure described above.

The difference between the first method according to the disclosure and the second method according to the disclosure resides within the generation of the at least one second medical information and the at least one third medical information, respectively. The second method according to the disclosure does not necessarily have to comprise a step of automatically exchanging information between the mobile communications device and the portable medical device. Thus, for the second method according to the disclosure, the user might manually input data into the mobile communications device for transmission to the medical care server. The user might obtain some medical information by simply reading an output value of the portable medical device and may manually input this value into the mobile communications device for transmission to the medical care server.

The software package downloaded from the server may comprise a software package for communication between the mobile communications device and the portable medical device and/or the communication software package for uploading the at least one third medical information from the mobile communications device to the medical care server. Thus, both methods according to the disclosure support the idea of mobile health care and home care.

Further, the disclosure includes the system for monitoring medical data, which can, e.g. be applied with the methods according to the disclosure disclosed above. The system comprises a portable medical device, a mobile communications device, and a download server, as described above. The portable medical device and the mobile communications device each comprise at least one interface for data transfer, such as for wireless data transfer, e.g. of the types described above. The mobile communications device and the download server comprise means for establishing a download link, such as a wireless download link, between the mobile communications device and the download server. The expression "means" may include hardware means and/or software means, e.g. means for transmitting data via a wireless telecommunications network, as well as suitable modem connections including software.

On the download server, a plurality of communication software packages for controlling data transfer, such as wireless data transfer, between a mobile communications device and a portable medical device are stored. These communication software packages may comprise communication software packages as described above with the method according to the disclosure.

Further, the mobile communications device and/or the download server comprise means for exchanging information on which type of mobile communications device and/or which type of portable medical device is used by the user, as well as means for choosing an appropriate communication software package from the plurality of communication software packages accordingly. The means for exchanging information on the type of mobile communications device and/or the type of portable medical device may include hardware and software means, such as memories for storing information on the type of mobile communications device and/or the type of portable medical device, may comprise a software offering a list of types of mobile communications devices and/or types of portable medical devices to the user, and/or may comprise means for automatic transmission of an information on the type of mobile communications device used by the user.

The system according to the disclosure may further comprise software means for performing one or both of the methods according to the disclosure as described above. Thus the disclosure includes a computer program comprising program means for performing one or both of the methods according to the disclosure as described above, while the computer program is being executed on a computer or a computer network, the computer or computer network being part of a mobile communications device, a download server, and/or a medical care server. The program means may be stored on storage medium readable to a computer. Further, the disclosure includes a storage medium, wherein a data structure is stored on the storage medium and wherein the data structure is adapted to perform one or both of the methods according to the description given above after having been loaded into a main and/or working storage of a computer or of a computer network, the computer or computer network being part of the mobile communications device, a download server, and/or a medical care server.

Furthermore, an embodiment of the disclosure includes a computer program product having program code means, wherein the program code means are stored on a storage medium, for performing one or both of the methods disclosed above. If the program code means are executed on a computer or on a computer network, the computer or computer network being part of a mobile communications device, a download server, and/or a medical care server. Therein, a computer program product is meant to be a tradable product. It may exist in any viable form, e.g. on paper and/or a computer-readable data carrier, and may be distributed via a computer network.

BRIEF DESCRIPTION OF THE DRAWINGS

For more complete understanding of the present disclosure, reference is established to the following description made in connection with accompanying drawings in which.

Figure 1:
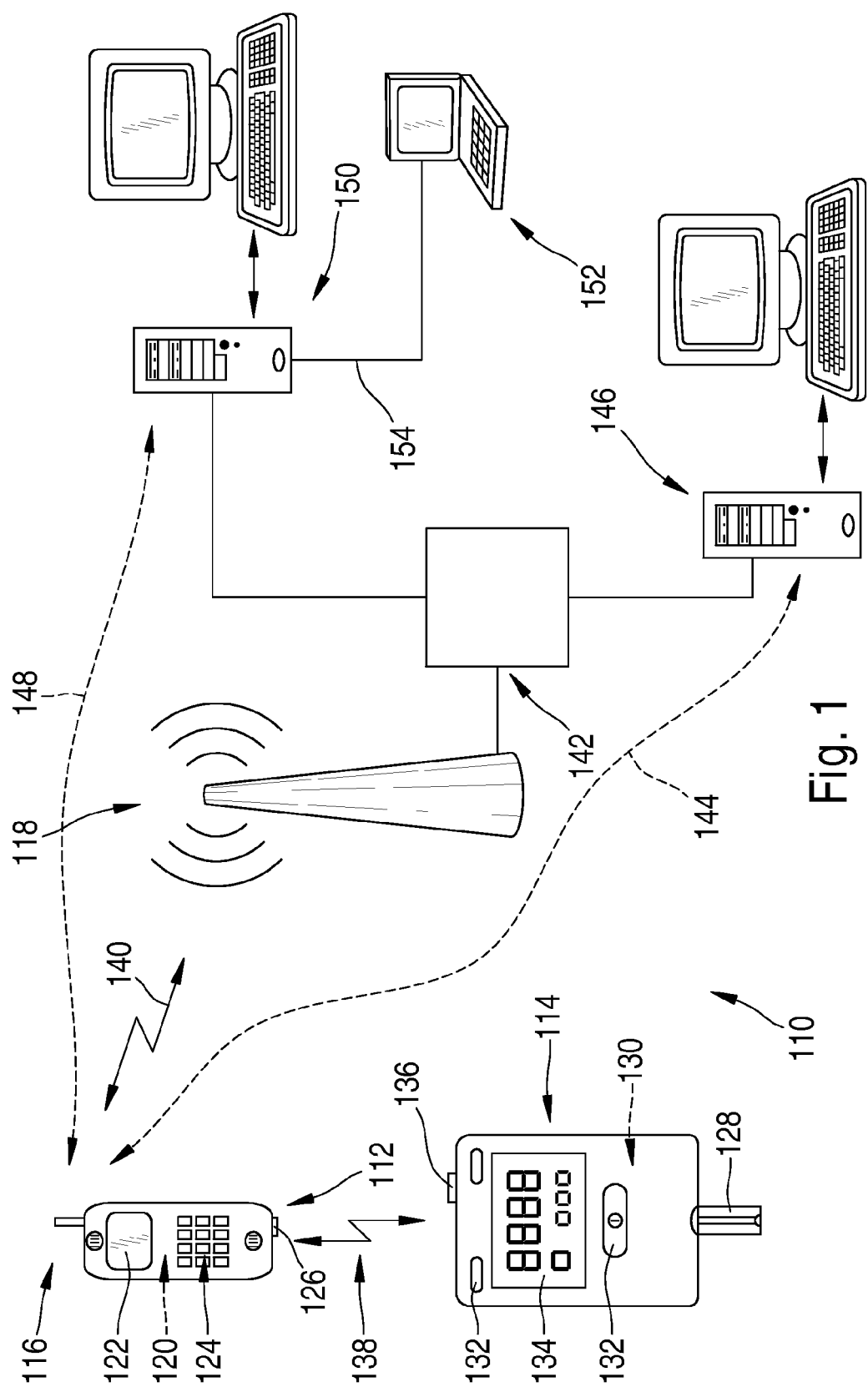
FIG. 1 shows a system for monitoring medical data using a cell phone and a blood glucose meter.

Although the drawings represent embodiments of various features and components according to the present disclosure, the drawings are not necessarily to scale and certain features may be exaggerated in order to better illustrate and explain the present disclosure. The exemplification set out herein illustrates embodiments of the disclosure, and such exemplifications are not to be construed as limiting the scope of the disclosure in any manner.

DETAILED DESCRIPTION OF EMBODIMENTS OF THE DISCLOSURE

For the purposes of promoting an understanding of the principles of the disclosure, reference will now be made to the embodiments illustrated in the drawings, which are described below. It will nevertheless be understood that no limitation of the scope of the disclosure is thereby intended. The disclosure includes any alterations and further modifications in the illustrated devices and described methods and further applications of the principles of the disclosure, which would normally occur to one skilled in the art to which the disclosure relates. Moreover, the embodiments were selected for description to enable one of ordinary skill in the art to practice the disclosure.

In FIG. 1, an exemplary embodiment of a system 110 for monitoring medical data is depicted. In this exemplary embodiment, the system 110 comprises a mobile phone 112 and a blood glucose meter 114. The mobile phone 112 comprises means 116 for transmitting and receiving data within a mobile communications network 118, e.g. a GSM network. Further, the mobile phone 112 comprises at least one microcomputer 120 with storage means, as well as a display 122 and keys 124. Further, the mobile phone 112 comprises a standard IrDA interface 126.

In the embodiment according to FIG. 1, the blood glucose meter 114 constitutes the portable medical device of the system 110. Other portable medical devices may be used additionally or alternatively. The blood glucose meter 114 in this example is a commercially available standard blood glucose meter for electrochemical blood glucose level measurements using a test strip 128. The blood glucose meter 114 comprises electronic components and at least one microcomputer 130 for evaluating the blood glucose level measurements. Further, the blood glucose meter 114 comprises several keys 132 as well as a display 134 for displaying medical information and other user information. Furthermore, the blood glucose meter 114 comprises a standard IrDA interface 136. As described above, other types of interfaces than IrDA interfaces 126, 136 may be used, such as e.g., interfaces using an interface cable for connecting the mobile phone 112 and the blood glucose meter 114. Nevertheless, the wireless IrDA interfaces 126, 136 allow for setting up a wireless infrared connection 138 between the mobile phone 112 and the blood glucose meter 114, thus avoiding the necessity for the patient to carry an interface cable.

Using the means 116 for wireless communication (also referred to herein as a "data transceiver"), mobile phone 112 is equipped to establish a wireless connection 140 with the mobile communications network 118. Thus, the mobile phone 112 is equipped to establish a connection with other networks connected to the mobile communications network 118, in the embodiment according to FIG. 1 with the internet 142, which is symbolically depicted in FIG. 1. Thus, the mobile phone 112 may establish a first connection with a download server 146 connected to the internet 142, and/or a second connection 148 to a medical care server 150. The download server 146 and the medical care server 150 do not necessarily have to be separate servers, but may belong to one and the same server system or a network of servers. Both servers 146 and 150 may comprise typical server means, which may comprise storage means, data base means, evaluation software means, and/or means for connecting to the internet 142, e.g. modem means. These typical server means are not explicitly depicted in FIG. 1.

The medical care server 150 in this exemplary embodiment according to FIG. 1 is connected to a doctor's unit 152, in FIG. 1 depicted as a mobile computer, such as a laptop. Alternatively or additionally, handheld computers or palmtops may be used, or even computer systems comprising a second mobile communications device such as a doctor's mobile phone. The connection between the doctor's unit 152 and the medical care server 150 may comprise a virtual private network (VPN) 154, which allows a fast and secure access from the doctor's unit 152 to data stored on the medical care server 150. Further, from the doctor's unit 152, even a connection may be made to the mobile phone 112, in order to transmit data to or receive data from the mobile phone 112 of the patient. Thus, a doctor may e.g. evaluate medical data sent by the mobile phone 112 and may in turn respond by sending data on potential medical counter actions, such as data on optimum medications.

Figure 2:
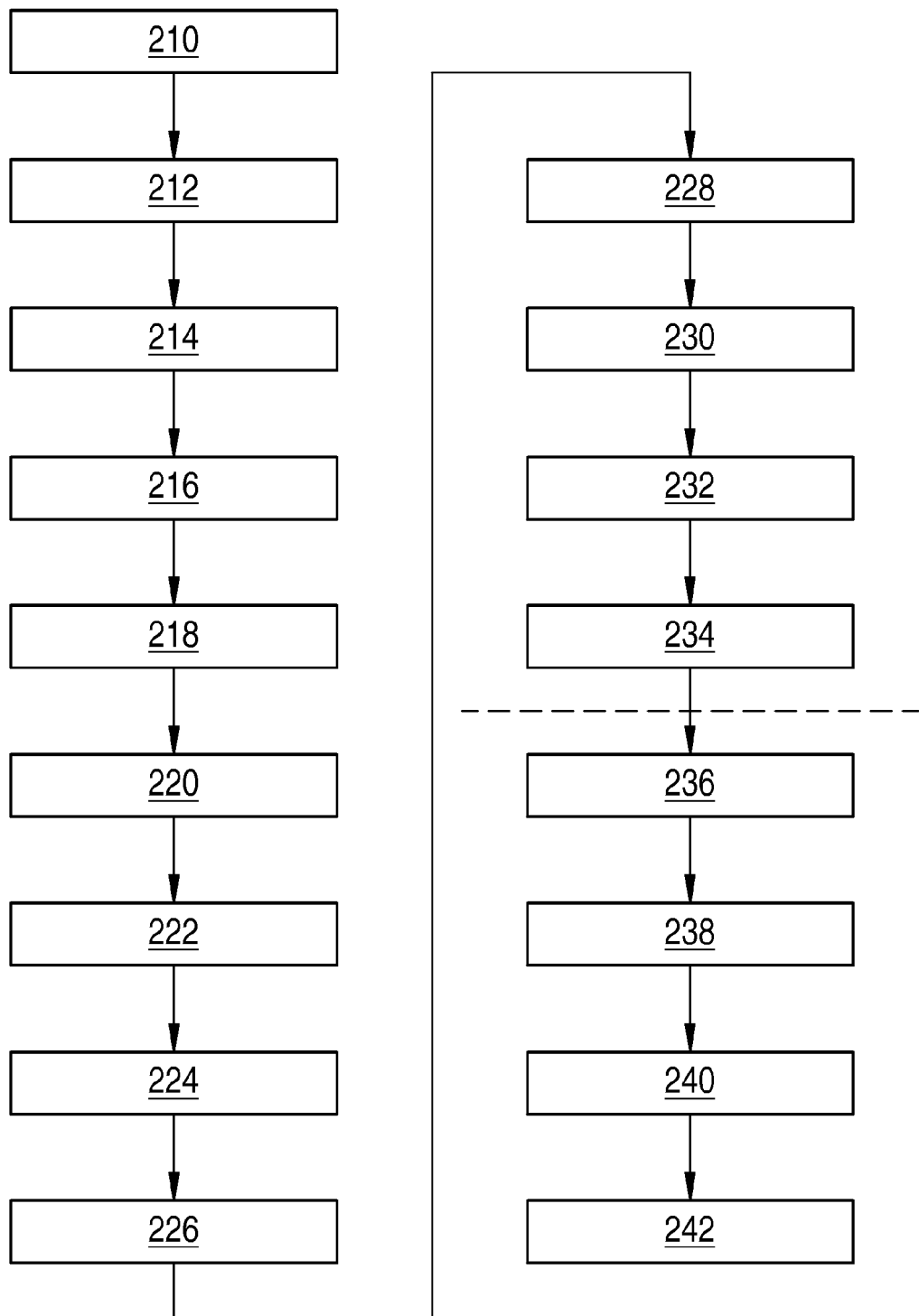
FIG. 2 shows an embodiment of the first method according to the disclosure for monitoring medical data.

In FIG. 2, an embodiment of the first method according to the disclosure as described above is depicted. As previously explained, the steps depicted in this figure do not necessarily have to be taken in the order depicted in FIG. 2, additional steps may be taken, and steps may be taken repeatedly or in parallel. In the following, the method according to FIG. 2 will be described, for exemplary purposes only, in connection with the system 110 according to FIG. 1. Nevertheless, the method may be applied to other systems for monitoring medical data.

In a first step 210, a patient (user) sends a first SMS via the mobile communications network 118 to a predetermined phone number. Thus, the user indicates his interest in starting a download process. This phone number may be the phone number of a service center, which, e.g. may comprise the download server 146 or may be part of the download server 146. As a response to this first SMS, in step 212 a WAP Push Message is sent to the patient's cell phone 112. As described above, this WAP Push Message may contain download information, such as the download address, e.g. the internet address of the download server 146. The WAP Push Message may be transmitted by the download server 146 or by any other system.

In step 214, the user opens the WAP Push Message, e.g. by simply selecting the message on the display 122 and activating a key 124. As a consequence, in step 216 the mobile phone 112 automatically navigates to the download server 146 and starts a download and setup process. In step 218, the information on the type of the user's mobile phone 112, such as an information on the mobile phone's 112 manufacturer and/or the model of the mobile phone 112, is automatically transmitted to the download server 146. Consequently, a software installed on the download server 146 narrows down the number of communication packages which are suited to be used by the patient.

In step 220, a list of types of blood glucose meters and/or other portable medical devices is presented to the patient, e.g. by transmitting this list from the download server 146 to the mobile phone 112 and by displaying this list on the display 122. The user selects the type of portable medical device, specifically the type of blood glucose meter 114 he intends to use, e.g. by selecting this type of blood glucose meter 114 from the list displayed on the display 122 and activating one specific key of the keys 124, e.g. an "Enter" key. Thus, a suitable communication software package stored on the download server 146 is selected, which allows for a communication between the mobile phone 112 and the blood glucose meter 114, e.g. via the infrared connection 138.

In step 224, permission is asked from the user to download the selected software package and to install the software package on the microcomputer 120 of the mobile phone 112. Consequently, if the user indicates his permission, e.g. by activating a predetermined key 124 of the mobile phone 112, the download from the download server 146 to the mobile phone 112 via the first connection 144 (download connection) is performed. This download may comprise, as indicated, the download of a communication software package allowing for a communication between the mobile phone 112 and the blood glucose meter 114. Further software packages may be downloaded, such as a software package allowing for communication between the mobile phone 112 and the medical care server 150, e.g. via the second connection 148. Further software packages may be downloaded, such as e.g. database software for monitoring medical data as well as other application software packages, e.g. software packages for (pre-)processing medical information and/or displaying this medical information on the display 122 of the mobile phone 112. Nevertheless, these application software packages may alternatively be downloaded in a separate process, e.g. from a separate download server 146.

In step 228, the software downloaded from the download server 146 is installed on the microcomputer 120 of the mobile phone 112. Again, this installation may be performed automatically, or may be initiated by the user, e.g. after giving a separate permission for installation. After performing the installation in step 228, the mobile phone 112 may communicate with the blood glucose meter 114 and may uni-directionally or bi-directionally, exchange information with the blood glucose meter 114. Further, the mobile phone 112 may be used in order to control several or all functions of the blood glucose meter 114. Further, optionally, as indicated above, after the installation in step 228, the mobile phone 112 may also be equipped to perform communication with the medical care server 150.

In step 230, the patient takes a blood glucose measurement using the blood glucose meter 114. Thus, the patient may apply a blood sample to the test strip 128 and may initiate the measurement using the keys 132 of the blood glucose meter 114. This measurement may be processed by the electronic components and the microcomputer 130 of the blood glucose meter 114, and the result of this measurement may be displayed on display 134 and/or stored in a memory and/or database of the blood glucose meter 114.

In step 232, the mobile phone 112 requests the transmission of a first medical information from the blood glucose meter 114 to the mobile phone 112. As described above, this first medical information may comprise results of the blood glucose measurement taken in step 230, or may comprise data derived from this blood glucose measurement. Other types of information may be included, such as e.g. the time of the blood glucose measurement taken in step 230. Further, this first medical information may comprise the data, such as data stored in a database of the blood glucose meter 114, e.g. medical data of previously taken blood glucose measurements. The first medical information is transmitted to the mobile phone 112 via the infrared connection 138. On the mobile phone 112, the first medical information is stored in a memory, and/or in a database, e.g. a database being stored on the microcomputer 120 (step 234). In step 234, additionally or optionally, other information may be stored in conjunction with this first medical information, such as e.g.

a time of the measurement and/or the data acquisition, as gained e.g. from an internal clock of the mobile phone 112.

The steps 210 to 234 as described above may constitute by themselves an embodiment of the first method according to the disclosure. The method may be optionally extended using the steps 236 to 242 depicted in FIG. 2. These steps allow for an exchange of information between the mobile phone 112 and the medical care server 150. Therefore, in step 236, the second connection 148 is established between the mobile phone 112 and the medical care server 150 via the mobile communications network 118 and the internet 142. This second connection 148 allows for exchanging a second medical information between the mobile phone 112 and the medical care server 150. In this example, this second medical information is exchanged in step 238 by sending a second SMS from the mobile phone 112 to the medical care server 150, the second SMS comprising the second medical information. Other types of information exchange may be used. Nevertheless, the use of SMS provides a fast and cost-efficient way of exchanging information. The second medical information, as explained above, may fully or partly comprise the first medical information. Additionally or alternatively, the first medical information may be processed on the microcomputer 120 of the mobile phone 112, and, thus, the second medical information may comprise processed or pre-processed derivatives of the first medical information. Other information may be included, such as a user authentication, e.g. a user's identification number and/or a pin number or a password.

In step 240 this second medical information is stored in a database on the medical care server 150. Thus, this second medical information is accessible for performing further operations, such as for applying further evaluation software algorithms to this second medical information. These evaluation software algorithms may be run on the medical server 150 or on separate computers, such as the doctor's unit 152. Warning functions may be implemented, such as warning functions generating a warning signal for the patient and/or the doctor or other medical personnel in case the second medical information and/or information derived from the second medical information indicates a critical status of the patient. In step 142, the second medical information and other information stored on the medical server 150 may be accessed via the VPN 154 from the doctor's unit 152. Thus, the doctor may monitor the patient's data and, in turn, react accordingly, such as by notifying the patient of optimum medication.

Figure 3:
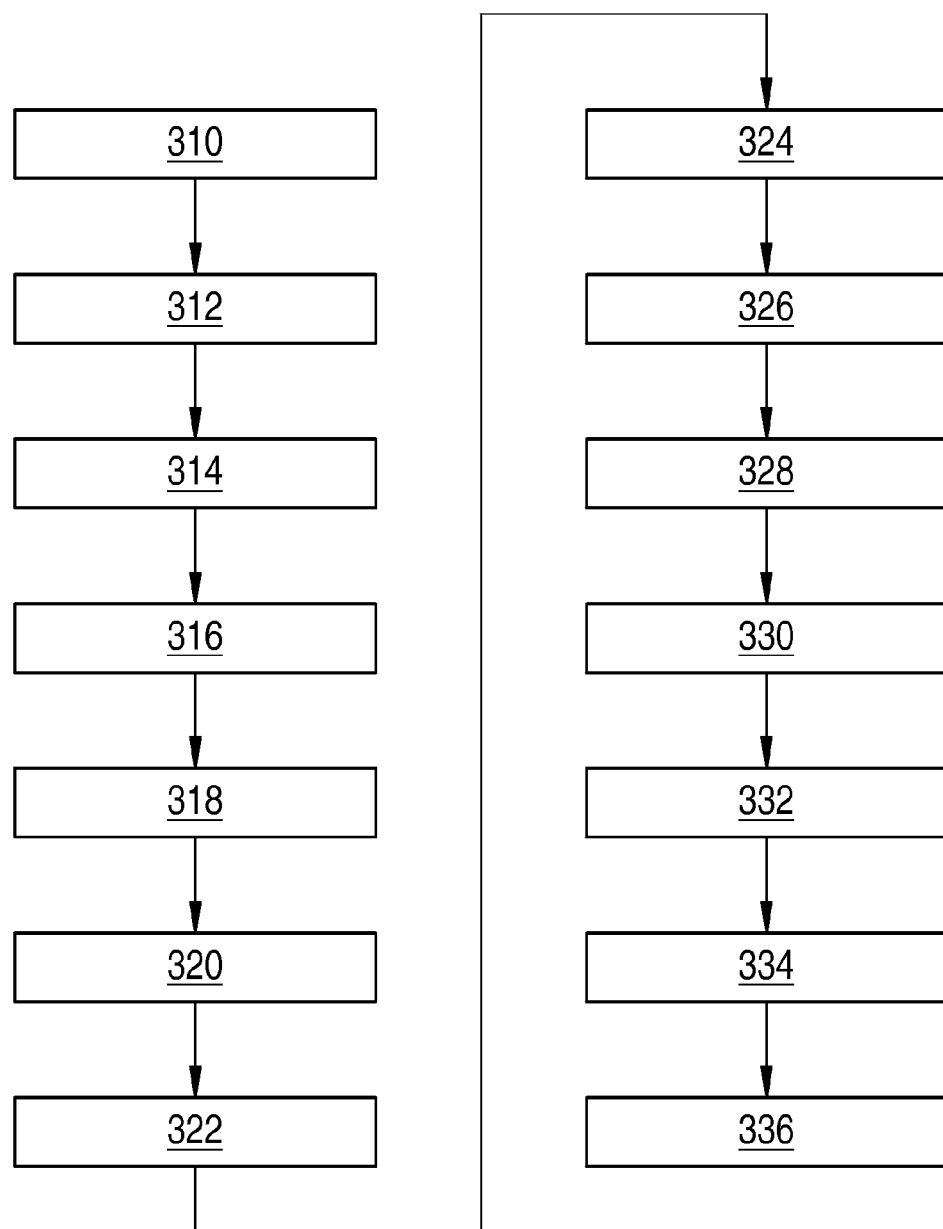
FIG. 3 shows an embodiment of the second method according to the disclosure for monitoring medical data.

In FIG. 3, an embodiment of the second method according to the disclosure is depicted. As explained above, this method does not necessarily require the mobile phone 112 and/or the blood glucose meter 114 to include interfaces 126, 136. In a first step 310, the patient initiates a download process by sending an SMS to a service center, e.g. the download server, similar to step 210 described above. In step 312, a WAP Push Message is sent to the patient's mobile phone 112, similar to step 212 described above. This WAP Push Message is opened by the user in step 314 (see step 214 above). Consequently, in step 316, the mobile phone 112 navigates to the download server 146. The type of the patient's mobile phone 112 is transmitted to the download server 146 in step 318 (see step 218 above). In steps 320 and 322, permission for download and installation is asked from the patient, and the download is initiated (see steps 224 and 226 above). Thus, in step 322, a communication software package is downloaded from the download server 146 to the mobile phone 112 which allows for establishing a second communication 148 between the mobile phone 112 and the medical care server 150. As indicated above, other software may be downloaded, such as database software or software comprising other algorithms for monitoring and/or processing medical data, such as evaluation or displaying software. The software is automatically installed on the mobile phone 112 in step 324, similarly to step 228 described above.

In step 326 the patient takes a measurement using the blood glucose meter 114 (see step 230 above). Following, in step 328, the user reads out measurement results from the display 134 of the blood glucose meter 114 and manually inputs this information into the mobile phone 112 using, e.g., the keys 124 or any other way of data input supported by the mobile phone 112, such as voice input or input via a touch pad. This data may e.g. be stored in the microcomputer 120 of the mobile phone 112, such as in a database. Further, in step 330, the user establishes the second connection 148 between the mobile phone 112 and the medical care server 150 (see step 236 above). Via this second connection 148, in step 332 an SMS is sent from the mobile phone 112 to the medical care server 150, the SMS containing a third medical information. Similar to the context of the description of step 238 in FIG. 2, this third medical information may fully or partially comprise the data of the manual data input of step 328 and/or data derived from this manual data input. Further data may be transmitted, such as a user authentication. In step 334, this third medical information is stored in a database within the medical care server 150 and, step 336 may be accessed by a doctor using the doctor's unit 152 and a VPN 154.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method for monitoring medical data, comprising:
a user establishing a download link between a mobile communications device and a download server that has access to a plurality of communication software packages stored on a memory;
the user selecting a communication software package from a subset of the plurality of communication software packages, wherein the communications software packages in the subset are compatible with the mobile communications device;
downloading the communication software package to the mobile communications device over the download link;
installing the communication software package on the mobile communications device;
wirelessly transferring medical data from a portable medical device to the mobile communications device using the downloaded and installed communication software package; and
uploading at least a portion of the medical data to a server from the mobile communications device.

2. The method as set forth in claim 1, further including the step of transmitting at least one Short Message Service (SMS) message from the mobile communications device to the server.

3. The method as set forth in claim 1, wherein the medical data uploaded to the server includes data selected from the group consisting of: glucose level information; cholesterol level information; coagulation information; measuring time; and insulin medication dose information.

4. A system for monitoring medical data, comprising:
a portable medical device including an interface configured for data transfer; and
a mobile communications device including an interface configured for wireless data transfer with the interface of the portable medical device, wherein the mobile communications device is configured to (i) establish a download link with a download server that has access to a plurality of software packages for controlling data transfer and (ii) exchange information relating to the type of mobile communications device and/or relating to the type of portable medical device being used;
wherein the mobile communications device is configured to:
present a subset of the software packages compatible with the type of mobile communications device and/or the type of portable medical device;
download a selected compatible software package and install the selected software package on the mobile communications device; and
upload to a server medical data wirelessly transferred from the portable medical device to the mobile communications device using the installed software package.

5. The system as set forth in claim 4, wherein the mobile communications device is selected from the group consisting of a mobile phone; a personal digital assistant (PDA); and a handheld computer.

6. The system as set forth in claim 4, wherein the portable medical device is selected from the group consisting of a glucose meter; a blood glucose meter; a cholesterol meter; a blood pressure meter; a coagulation meter; and an insulin pump.

7. The system as set forth in claim 4, wherein the interface for data transfer is selected from the group consisting of an infrared data transfer interface; a radio frequency data transfer interface; and a near field communication (NFC) interface.

8. The method as set forth in claim 1, wherein the software packages of the plurality of communication software packages are each configured for uploading data from the mobile communications device to the server.

9. The method as set forth in claim 1, wherein the step of wirelessly transferring medical data from the portable medical device to the mobile communications device uses radio frequency data transfer.

10. The method as set forth in claim 9, wherein the radio frequency transfer comprises Bluetooth data transfer.

11. The system of claim 4, wherein the interface of the portable medical device and the interface of the mobile communications device are configured to exchange data via radio frequency data transfer.

12. The system of claim 11, wherein the radio frequency data transfer comprises Bluetooth data transfer.

13. The system as set forth in claim 7, wherein the at least one interface for data transfer comprises Bluetooth data transfer.

14. The method as set forth in claim 1, wherein each of the software packages of the plurality of communication software packages are configured for data transfer between a mobile communications device and a portable medical device.

15. The method as set forth in claim 14, wherein the subset consists of a single software communication package.

16. The method as set forth in claim 1, wherein the subset consists of a single software communication package.

17. The method as set forth in claim 1, wherein the medical data uploaded to the server includes glucose level information.

\* \* \* \* \*